(12) United States Patent
Peyman

(10) Patent No.: US 8,162,927 B2
(45) Date of Patent: *Apr. 24, 2012

(54) METHOD AND APPARATUS FOR ACCOMMODATING INTRAOCULAR LENS

(75) Inventor: Gholam A. Peyman, New Orleans, LA (US)

(73) Assignee: Gholam A. Peyman, Sun City, AZ (US)

( * ) Notice: Subject to any disclaimer, the term of this patent is extended or adjusted under 35 U.S.C. 154(b) by 1643 days.

This patent is subject to a terminal disclaimer.

(21) Appl. No.: 11/189,044

(22) Filed: Jul. 25, 2005

(65) Prior Publication Data

US 2006/0084949 A1    Apr. 20, 2006

Related U.S. Application Data

(63) Continuation-in-part of application No. 10/993,169, filed on Mar. 3, 2005, now abandoned, which is a continuation-in-part of application No. 10/958,826, filed on Oct. 4, 2004, now abandoned, which is a continuation-in-part of application No. 10/272,402, filed on Oct. 17, 2002, now Pat. No. 7,001,374, which is a continuation-in-part of application No. 10/091,444, filed on Mar. 7, 2002, now Pat. No. 6,949,093, which is a continuation-in-part of application No. 09/532,516, filed on Mar. 21, 2000, now Pat. No. 6,436,092.

(51) Int. Cl.
*A61F 9/02* (2006.01)
(52) U.S. Cl. ............................................ 606/4; 128/898
(58) Field of Classification Search .................. 606/4–6, 606/10–15; 623/6.11–6.24, 6.27–6.56, 6, 623/61
See application file for complete search history.

(56) References Cited

U.S. PATENT DOCUMENTS 4,563,565 A    1/1986 Kampfer et al.
(Continued)

FOREIGN PATENT DOCUMENTS

WO    01/82815    11/2001

OTHER PUBLICATIONS

Karin R. Sletten, MD et al.; Experimental Science, "An In Vivo Model of Femtosecond Laser Intrastromal Refractive Surgery", Ophthalmic Surgery and Lasers, Nov./Dec. 1999, vol. 30, No. 9, pp. 742-749.

(Continued)

*Primary Examiner* — David Shay
(74) *Attorney, Agent, or Firm* — Wenderoth, Lind & Ponack, L.L.P.

(57) ABSTRACT

A method of replacing a natural lens in an eye is presented. The method includes removing the natural lens while leaving the capsular bag substantially intact, removing a portion of the capsular bag along the main optical axis, and placing biodendrimer within the capsular bag. Placing biodendrimer within the capsular bag can include placing a mixture of biodendrimer and at least one other material within the capsular bag. Biodendrimer can be approximately fifty percent of the mixture. The method can also include inserting an artificial bag within the capsular bag, injecting a synthetic material into the artificial bag to form an artificial lens, the synthetic material having loose monomers and a polymerization initiator so that the synthetic material changes its volume when exposed to an energy source, and selectively exposing portions of the artificial lens to an energy source to alter the refractive properties of the artificial lens.

22 Claims, 12 Drawing Sheets

U.S. PATENT DOCUMENTS

| | | | |
|---|---|---|---|
| 4,575,373 A | 3/1986 | Johnson | |
| 4,676,790 A | 6/1987 | Kern | |
| 4,685,921 A * | 8/1987 | Peyman | 623/6.13 |
| 4,702,865 A | 10/1987 | Koziol et al. | |
| 4,718,418 A | 1/1988 | L'Esperance, Jr. | |
| 4,840,175 A | 6/1989 | Peyman | |
| 4,892,543 A | 1/1990 | Turley | |
| 4,976,709 A | 12/1990 | Sand | |
| 4,994,058 A | 2/1991 | Raven et al. | |
| 5,098,444 A | 3/1992 | Feaster | |
| 5,120,121 A | 6/1992 | Rawlings et al. | |
| 5,151,098 A | 9/1992 | Loertscher | |
| 5,196,027 A | 3/1993 | Thompson | |
| 5,201,762 A | 4/1993 | Hauber | |
| 5,326,348 A * | 7/1994 | Nordan | 623/6.24 |
| 5,336,261 A | 8/1994 | Barrett et al. | |
| 5,476,515 A | 12/1995 | Kelman et al. | |
| 5,480,427 A | 1/1996 | Kelman et al. | |
| 5,527,524 A | 6/1996 | Tomalia et al. | |
| 5,607,472 A | 3/1997 | Thompson | |
| 5,647,865 A | 7/1997 | Swinger | |
| 5,722,971 A * | 3/1998 | Peyman | 606/5 |
| 5,824,086 A | 10/1998 | Silvestrini | |
| 5,876,442 A | 3/1999 | Lipshitz et al. | |
| 5,919,185 A | 7/1999 | Peyman | |
| 5,928,283 A | 7/1999 | Gross et al. | |
| 6,001,386 A | 12/1999 | Ashton et al. | |
| 6,066,171 A | 5/2000 | Lipshitz et al. | |
| 6,102,946 A | 8/2000 | Nigam | |
| 6,197,019 B1 | 3/2001 | Peyman | |
| 6,357,875 B1 | 3/2002 | Herrick | |
| 6,358,280 B1 | 3/2002 | Herrick | |
| 6,361,560 B1 | 3/2002 | Nigam | |
| 6,399,734 B1 * | 6/2002 | Hodd et al. | 623/6.11 |
| 6,413,276 B1 | 7/2002 | Werblin | |
| 6,436,092 B1 | 8/2002 | Peyman | |
| 6,450,642 B1 | 9/2002 | Jethmalani et al. | |
| 6,533,769 B2 * | 3/2003 | Holmen | 623/6.56 |
| 6,596,026 B1 | 7/2003 | Gross et al. | |
| 6,702,807 B2 | 3/2004 | Peyman | |
| 6,749,632 B2 | 6/2004 | Sandstedt et al. | |
| 6,813,097 B2 | 11/2004 | Jethmalani et al. | |
| 6,824,266 B2 | 11/2004 | Jethmalani et al. | |
| 6,851,804 B2 | 2/2005 | Jethmalani et al. | |
| 6,986,763 B2 | 1/2006 | Holmen | |
| 2002/0016629 A1 | 2/2002 | Sandstedt et al. | |
| 2002/0042004 A1 | 4/2002 | Sandstedt et al. | |
| 2002/0107566 A1 | 8/2002 | Nigam | |
| 2002/0138070 A1 | 9/2002 | Peyman | |
| 2002/0167735 A1 | 11/2002 | Jethmalani et al. | |
| 2002/0169505 A1 | 11/2002 | Jethmalani et al. | |
| 2003/0014021 A1 | 1/2003 | Holmen | |
| 2003/0048411 A1 | 3/2003 | Jethmalani et al. | |
| 2003/0090013 A1 | 5/2003 | Jethmalani et al. | |
| 2003/0090624 A1 | 5/2003 | Jethmalani et al. | |
| 2003/0093150 A1 | 5/2003 | Jethmalani et al. | |
| 2003/0128336 A1 | 7/2003 | Jethmalani et al. | |
| 2003/0151825 A1 | 8/2003 | Bielawski et al. | |
| 2003/0151831 A1 | 8/2003 | Sandstedt et al. | |
| 2003/0176521 A1 | 9/2003 | Jethmalani et al. | |
| 2004/0086479 A1 * | 5/2004 | Grinstaff et al. | 424/78.17 |
| 2005/0099597 A1 | 5/2005 | Sandstedt et al. | |

OTHER PUBLICATIONS

Griffith et al., "Functional Human Corneal Equivalents Constructed from Cell Lines", Science, vol. 286, Dec. 10, 1999, pp. 2169-2172.

Yamauchi et al.; "Cultivation of fibroblast cells on keratin-coated substrata", Polymers for Tissue Engineering, pp. 329-340, VSP 1998.

Ijima et al.; "Formation of spherical multicellular aggregate (spheroid) of animal cells in the pores of polyurethane form as a cell culture substratum and its application to a hybrid artificial liver", Polymers for Tissue Engineering, pp. 273-286, VSP 1998.

Cao et al.; "Comparative study of the use of poly(glycolic acid), calcium alginate and pluronics in the enginnering of autologous porcine cartilage", Polymers for Tissue Engineering, pp. 315-327, VSP 1998.

Jose I. Barraquer, MD, "Keratomileusis and keratophakia in the surgical correction of aphakia", pp. 270-289, published before Mar. 21, 2000.

International Search Report.

* cited by examiner

METHOD AND APPARATUS FOR ACCOMMODATING INTRAOCULAR LENS

RELATED APPLICATIONS

This application is a continuation-in-part of application Ser. No. 10/993,169 filed Mar. 3, 2005 now abandoned and titled "Adjustable Optical Element With Multizone Polymerization," which is a continuation-in-part of application Ser. No. 10/958,826 filed Oct. 4, 2004 now abandoned and titled "Adjustable Intraocular Lens for Insertion into the Capsular Bag," which is a continuation-in-part of application Ser. No. 10/272,402, filed Oct. 17, 2002, now U.S. Pat. No. 7,001,374 and titled "Adjustable Inlay With Dual Zone Polymerization," which is a continuation-in-part of application Ser. No. 10/091,444, filed Mar. 7, 2002, now U.S. Pat. No. 6,949,093 and titled "An Adjustable Universal Implant Blank for Modifying Corneal Curvature and Methods of Modifying Corneal Curvature Therewith", which is a continuation-in-part of application Ser. No. 09/532,516, filed Mar. 21, 2000, and titled "An Adjustable Universal Implant Blank for Modifying Corneal Curvature and Methods of Modifying Corneal Curvature Therewith", now U.S. Pat. No. 6,436,092. The entire contents of each of the above-referenced applications is incorporated herein by reference.

BACKGROUND

An eye can have various disorders which affect the crystalline lens of the eye. One of the most common disorders is cataracts, which is a clouding of the crystalline lens. The conventional treatment for cataracts is removal of the crystalline lens and replacement of the lens with an artificial or intraocular lens (IOL).

Once an IOL is implanted, however, it generally has a fixed refractive power. This presents a problem with respect to both far and near vision. With respect to far vision, the diopter power of the IOL is generally not capable of perfect vision—i.e. 20/20. This problem is due to the fact that the refractive power of the IOL must be chosen prior to implantation and thus can only be approximated. Since the diopter power can only be approximated, most patients will require at least a ±1.00 diopter power correction along the optical path to provide perfect vision. With respect to near vision, an artificial lens results in a loss of accommodation (i.e., the process of focusing the eye between far objects and near objects).

In an attempt to avoid loss of accommodation, a technique has been developed that involves removing the crystalline lens and leaving the capsular bag that holds the crystalline lens substantially intact. Once the lens has been removed, a new lens is created in situ by filling the capsular bag with a liquid material and polymerizing or curing the liquid to form an IOL in situ. The newly formed lens has characteristics that approximate the function of a crystalline lens. By leaving the capsular bag substantially intact, the newly formed IOL will be able to focus the eye between near and far objects better than if the capsular bag is removed since the capsular bag is attached to the interior of the eye by the zonular ligaments.

This in situ replacement of a crystalline lens has been referred to as a phaco-ersatz procedure. U.S. Pat. No. 6,598,606 B2 to Terwee et al. discloses a method of forming an IOL in situ using a photo-curable polymerizable material, and is herein incorporated by reference in its entirety.

One drawback to the phaco-ersatz procedure described in the Terwee patent is that the shape of the lens, after creation, is not particularly controllable. That is, the shape of the lens is largely dictated by the shape of the capsular bag, and a surgeon has little control over the shape of the lens. Consequently, the newly formed lens is unlikely to provide the exact refractive power necessary to provide perfect vision. Therefore, as with a conventional IOL at least a ±1.00 diopter power correction will be required to obtain perfect vision. Furthermore, the newly formed lens will not compensate for any optical aberrations located elsewhere in the eye, such as astigmatism in the cornea.

SUMMARY

A method of replacing a natural lens in an eye is presented. The method includes removing the natural lens while leaving the capsular bag substantially intact, removing a portion of the capsular bag along the main optical axis, and placing biodendrimer within the capsular bag. Placing biodendrimer within the capsular bag can include placing a mixture of biodendrimer and at least one other material within the capsular bag. Biodendrimer can be approximately fifty percent of the mixture.

The method can also include inserting an artificial bag within the capsular bag, injecting a synthetic material into the artificial bag to form an artificial lens, the synthetic material having loose monomers and a polymerization initiator so that the synthetic material changes its volume when exposed to an energy source, and selectively exposing portions of the artificial lens to an energy source to alter the refractive properties of the artificial lens. The energy source can be light. Placing biodendrimer within the capsular bag can include injecting biodendrimer into the artificial bag. Further, placing biodendrimer within the capsular bag can include injecting biodendrimer between the artificial bag and the capsular bag. Also, the artificial bag can include biodendrimer.

The method can also include exposing substantially the entire artificial lens to an energy source to polymerize substantially all of the loose monomers, thereby fixing the refractive power of the synthetic material. Further, inserting an artificial bag can include inserting an artificial bag having a first internal chamber and a second internal chamber. The first internal chamber can include a polymerized material, and injecting a synthetic material into the artificial bag can include injecting the synthetic material into the second chamber. Further, the polymerized material can be biodendrimer. Also, placing biodendrimer within the capsular bag can include injecting biodendrimer into said second chamber. Also, a portion of the artificial bag can include a polymerized material.

The method can also include coating a portion of the capsular bag with a synthetic material, the synthetic material having loose monomers and a polymerization initiator so that the synthetic material changes its volume when exposed to an energy source. Placing biodendrimer within the capsular bag can include filling the remaining portion of the capsular bag with a material, wherein the material includes biodendrimer. Further, the method can include inserting a lens into the capsular bag, the lens including loose monomers and a polymerization initiator so that the synthetic material changes its volume when exposed to an energy source. Placing biodendrimer within the capsular bag can include filling the remaining portion of the capsular bag with a material, wherein the material includes biodendrimer.

An intraocular lens is also presented. The intraocular lens includes a flexible capsule adapted to be inserted into the natural lens capsular bag, wherein the flexible capsule includes biodendrimer, a polymerized portion positioned within said flexible capsule, and an unpolymerized material positioned within said flexible capsule. The unpolymerized material has loose monomers and a polymerization initiator so that the unpolymerized material changes its volume when exposed to an energy source. Further, the polymerized portion can include biodendrimer.

Additional features and advantages of the present invention are described in, and will be apparent from, the following Detailed Description of the Invention and the figures.

DETAILED DESCRIPTION OF THE PREFERRED EMBODIMENTS

Figure 1:
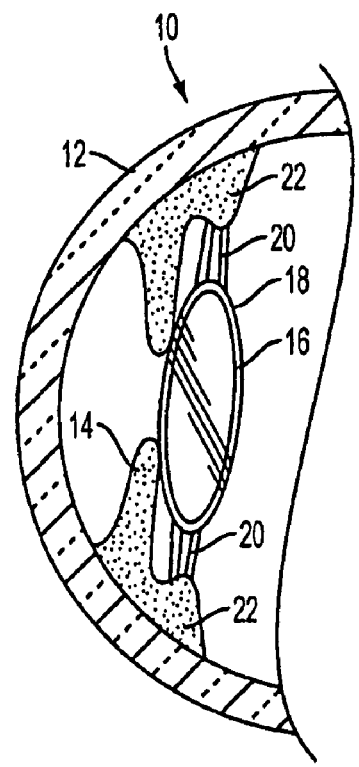
FIG. 1 is a side elevational view in section taken through the center of an eye showing the cornea, pupil, crystalline lens, and capsular bag.

Referring initially to FIG. 1, a normal eye 10 has a cornea 12, an iris 14, and a crystalline lens 16. The crystalline lens 16 is contained within a capsular bag 18 that is supported by zonules 20. The zonules 20, in turn, are connected to the ciliary muscle 22. According to Helmholz's theory of accommodation, upon contraction of the ciliary muscle 22, the tension on the zonules 20 is released. The elasticity of the lens causes the curvature of the lens 16 to increase, thereby providing increased refractive power for near vision. Conversely, during dis-accommodation, the ciliary muscle 22 is relaxed, increasing the tension on the zonules 20 and flattening the lens 16 to provide the proper refractive power for far vision.

Figure 2:
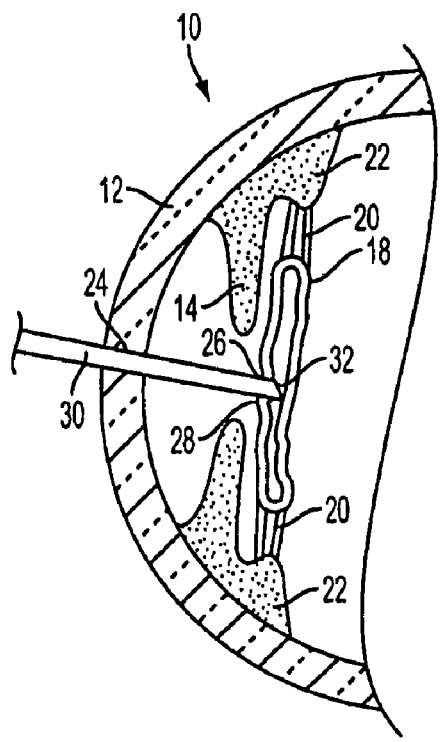
FIG. 2 is a side elevational view in section of the eye shown in FIG. 1 showing the capsular bag after removal of the crystalline lens.

To replace the crystalline lens in accordance with the method of the present invention, the first step is to remove the existing lens. Preferably, one or more of the materials that replace the crystalline lens include biodendrimer. As illustrated in FIG. 2, the lens is removed using any technique which allows removal of the lens through a relatively small incision, preferably about a 1-2 mm incision. The preferred method is to create a relatively small incision 24 in the cornea 12 and then perform a capsulorhexis to create an opening 26 into the anterior side 28 of the capsular bag 18. An ultrasonic probe 30 is inserted into the capsular bag 18 through the opening 26. The probe's vibrating tip 32 emulsifies the lens 16 into tiny fragments that are suctioned out of the capsular bag by an attachment on the probe tip (not shown). Alternatively, the lensectomy may be performed by laser phacoemulsification or irrigation and aspiration.

Once the crystalline lens 16 has been removed, the capsular bag 18 is treated to help prevent a phenomenon known as capsular opacification. Capsular opacification is caused by the proliferated growth of the epithelial cells on the lens capsule. This growth can result in the cells covering all or a substantial portion of the front and rear surfaces of the lens capsule, which can cause the lens capsule to become cloudy and thus adversely affect the patient's vision. These cells can be removed by known techniques, such as by scraping away the epithelial cells; however, it is often difficult to remove all of the unwanted cells. Furthermore, after time, the unwanted cells will typically grow back, requiring further surgery. To prevent capsular opacification, the capsular bag 18 is treated to eliminate the proliferated growth of epithelial cells, as described below.

Figure 3:
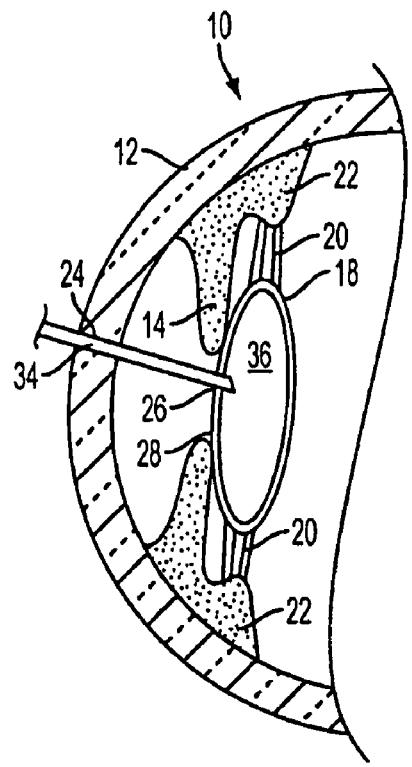
FIG. 3 is a side elevational view in section of the eye shown in FIG. 2 showing the treatment of the interior of the capsular bag with a liquid to prevent capsular opacification.

As seen in FIG. 3, one method of treating the epithelial cells to prevent capsular opacification is to use a cannula 34 to introduce a warm liquid 36 (preferably about <60° C.) into the capsular bag 18, filling the capsular bag 18. The liquid contains a suitable chemical that kills the remaining lens cells in the capsular bag and also cleans the interior of the capsular bag. Suitable chemicals, as well as other suitable methods of treatment that prevent capsular opacification are disclosed in U.S. Pat. No. 6,673,067 to Peyman, which is herein incorporated by reference in its entirety.

After treating the capsular bag to prevent capsular opacification, the capsular bag is filled with a synthetic, injectable material. The synthetic material is preferably a silicone based material which is un-polymerized. The material has a viscosity between about 10 centistokes (cSt) and about 10,000 centistokes at body temperature (or about 37° C.) so that it may be injected into the body though a cannula. The synthetic material contains loose monomers and can contain an initiator that initiates polymerization of the loose monomers. In a preferred embodiment, the initiator is a photoinitiator so that when the material is exposed to the proper wavelength of light, preferably blue light, the initiator causes the loose monomers to polymerize. Initiators responsive to other sources of energy, such as heat or chemicals, may be used if desired.

The polymerization of the monomers caused by the initiators results in a lower concentration of monomers in the polymerized area. Through the principle of diffusion, loose monomers therefore migrate to the polymerized area, causing the polymerized area to swell. Suitable materials, and a more detailed discussion of their method of operation, are disclosed in U.S. Pat. No. 6,721,043 B2 to Platt et al., U.S. Pat. No. 6,749,632 B2 to Sandstedt et al., and U.S. Pat. App. No. 2003/0174375 A1 to Jethmalani et al, all of which are herein incorporated by reference in their entirety.

Figure 4:
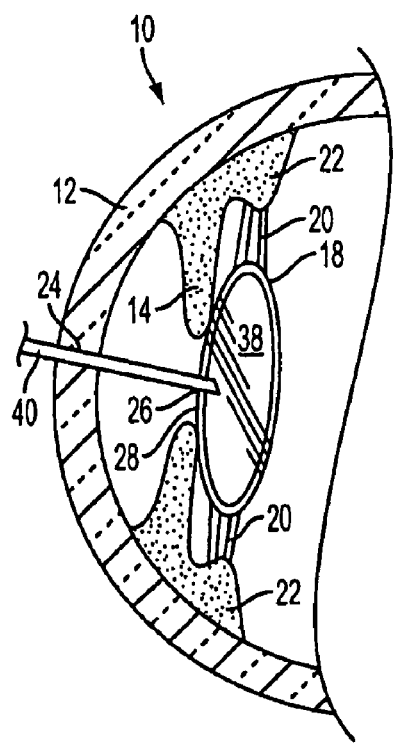
FIG. 4 is a side elevational view in section of the eye shown in FIG. 3 showing the injection of a synthetic material with free monomers into the capsular bag using a fiber optic tube.
Figure 5:
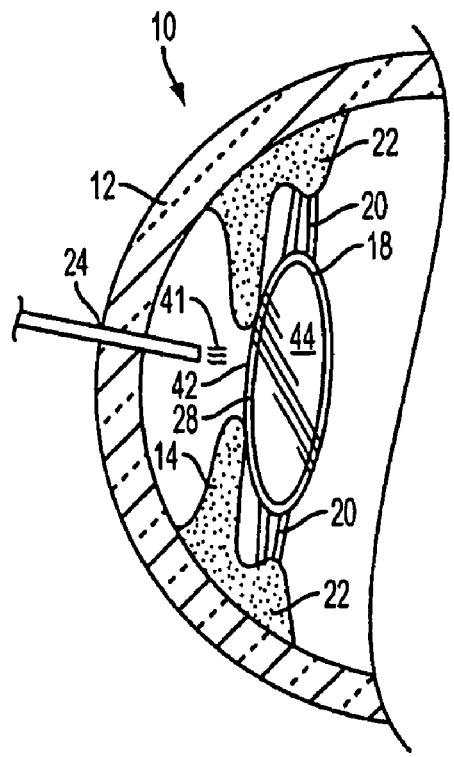
FIG. 5 is a side elevational view in section of the eye shown in FIG. 4 showing the removal of the fiber optic tube and curing of the injected material at the injection site to form an artificial lens.

As shown in FIG. 4, the synthetic material 38 is injected into the capsular bag 18 using a hollow tube 40. The synthetic material 38 is preferably a mixture that includes biodendrimer and an un-polymerized material; however, the synthetic material 38 can be any suitable material. Preferably, the un-polymerized material is an un-polymerized silicone based material; however, the material can be any suitable un-polymerized material. Further, the synthetic material 38 is preferably a mixture of approximately 50% biodendrimer and approximately 50% an un-polymerized material; however, the synthetic material 38 can have any suitable percentage of biodendrimer, un-polymerized material or other material.

Returning to FIG. 4, preferably, the tube 40 is a hollow fiber optic (i.e. light conducting) tube and the injection is made through the same opening 26 that was created to remove the crystalline lens 16. The amount of material that is injected into the capsular bag is chosen so that it closely approximates the desired refractive power of the original, natural lens. Any remaining fluid that is present in the capsular bag prior to injection of the synthetic material 38 can either be aspirated through another hole in the capsular bag, or can simply be allowed to leak through the edges of the capsular bag.

After the desired amount of material has been injected into the capsular bag 18, light 41 is transmitted through the light conducting tube 40 at the same time the tube is withdrawn from the opening 26 to the capsular bag 18. The light 41 is at the appropriate wavelength to initiate polymerization of the liquid material. Thus, when the tube 40 is removed, the polymerized liquid material forms a polymerized plug 42 that seals the opening 26 into the capsular bag 18, trapping the remaining liquid material inside the capsular bag. It should be noted that the liquid material can be polymerized in any suitable manner. At this point, the capsular bag 18 is filled with a liquid, photo-sensitive material, thereby forming an artificial lens 44.

Figure 6:
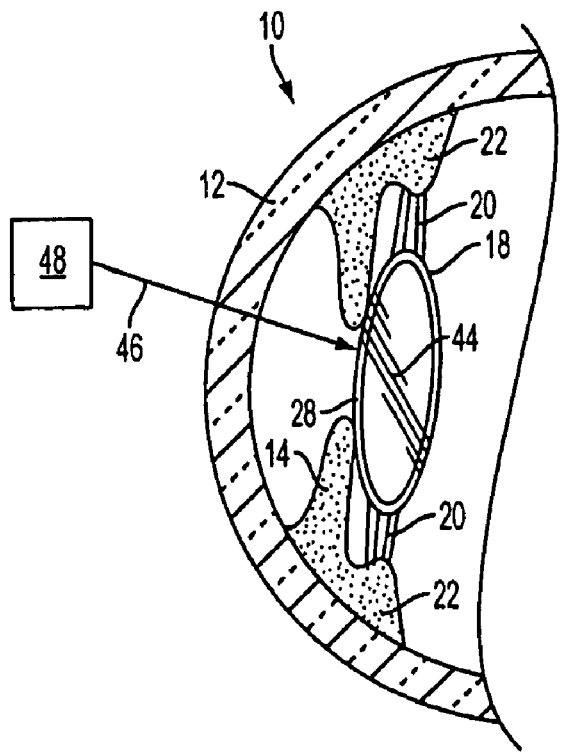
FIG. 6 is a side elevational view in section of the eye shown in FIG. 5 showing the adjustment of the artificial lens using a laser.

After creating the artificial lens 44, a suitable period of time, such as a few minutes, hours or days, is allowed to elapse so that the eye heals and the refractive power of the eye stabilizes. The eye is then measured to determine if there are any remaining optical aberrations in the eye that need to be corrected. The eye can be measured using, for example, wavefront sensor technology. If there are any errors which need to be corrected, the artificial lens 44 can be adjusted by exposing the lens 44 to light 46, which is generated by a light source 48 (FIG. 6). Light 46 is applied in a predetermined pattern to modify the refractive properties of the lens 44 as desired to create perfect, or 20/20, far vision.

Figure 7:
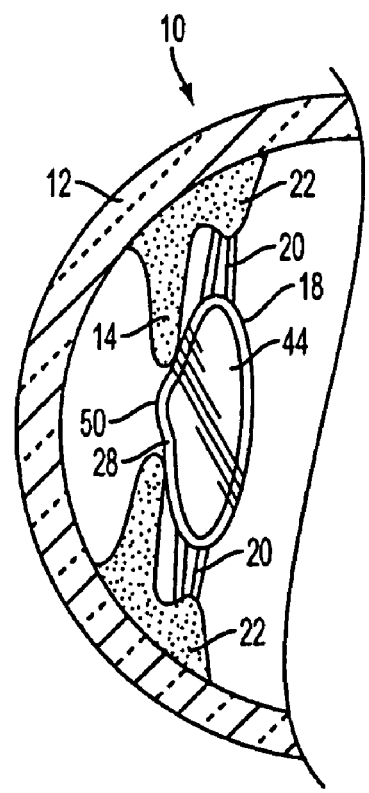
FIG. 7 is a side elevational view in section of the eye shown in FIG. 5 in which the central area of the artificial lens has increased in volume in response to the application of the light.
Figure 8:
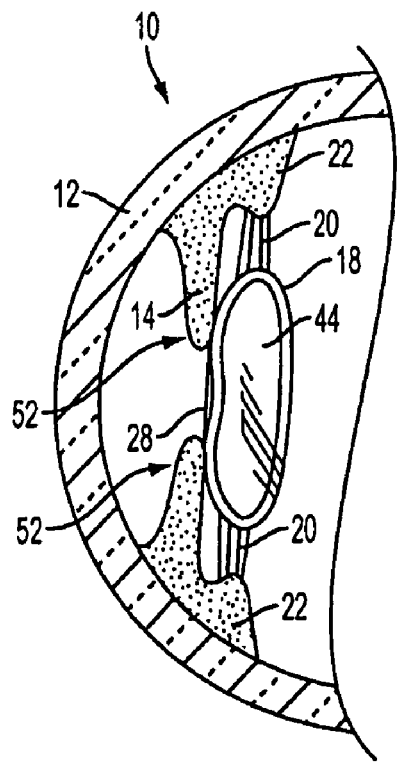
FIG. 8 is a side elevational view in section of the eye shown in FIG. 5 in which the peripheral area of the artificial lens has increased in volume in response to the application of the light.

For example, referring to FIG. 7, if the surgeon determines that additional plus dioptic power is needed, the surgeon can selectively polymerize the central portion 50 of the artificial lens 44 by aiming a light with the appropriate wavelength through the cornea 12 towards the central portion 48 of the lens. As discussed above, this will cause the central portion 48 of the lens to swell, thereby providing increased plus dioptic power. Conversely, if the surgeon wishes to lower the plus dioptic power of the lens, the surgeon can direct blue light towards the periphery 52 of the lens. This will cause the periphery 52 to swell, thereby flattening the lens 44 and reducing the amount of plus dioptic power of the lens 44. Likewise, various portions of the lens may be irradiated with the light to introduce corrections for other optical aberrations, such as astigmatisms. Furthermore, the lens can be shaped, such that it forms a multifocal lens. The lens can have different portions that have different refractive properties to allow the eye to focus on both near and far objects. For example, the differing refractive properties can be substantially ring-shaped concentric to each other or positioned at any other place or position on the lens.

The adjustment process may be repeated until the desired corrective capabilities have been programmed into the lens 44. Once satisfied with the lens, the entire lens 44 is irradiated with an appropriate wavelength of light to polymerize the entire unpolymerized material in the lens, thereby fixing the refractive power of the lens.

After this final polymerization of the lens, the lens 44 takes on a gel-like consistency that approximates the function of a crystalline lens. The lens 44 therefore is capable of providing accommodation. That is, in the method of the present invention, the capsular bag 18 has been left substantially intact, and the zonules 20 and ciliary muscle 22 have not been damaged. Consequently, upon contraction or relaxation of the ciliary muscle 22, the artificial lens 44 functions like a natural lens, since the polymerized material has a gel like consistency. Therefore, lens 44 can become rounder or flatter like a natural lens to provide accommodation for near vision.

Furthermore, accommodation takes place because the contraction and relaxation of the ciliary muscle 22 moves the lens forward and backward (i.e. closer to and further from the retina). This movement of the lens also produces accommodation.

Figure 9:
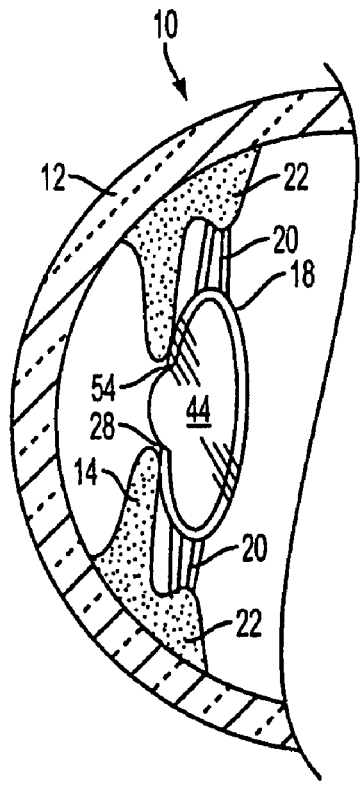
FIG. 9 is a side elevational view in section of the eye shown in FIG. 5 in which an anterior capsulotomy has been performed to allow the central area of the artificial lens to expand.

FIG. 9 shows an additional method of changing the refractive power of the implanted artificial lens 44. In FIG. 9, after the lens 44 has been polymerized to a gel-like consistency, an anterior capsulotomy is performed to remove the central portion of the anterior side 28 of the capsular bag 18. This allows the gel-like lens 44 to bulge slightly forward through the capsulotomy 54 to add additional dioptic power to the lens during accommodation.

FIGS. 10-18 show an another embodiment of the present invention, wherein an IOL 59 is formed by an artificial capsular bag or capsule 60 that is positioned within the original or natural capsular bag 18.

This artificial capsular bag 60 is preferably formed from biodendrimer or a mixture of biodendrimer and at least one other material; however, artificial bag 60 can be formed from silicon or any other suitable transparent polymer. Preferably, when biodendrimer is used, it is approximately 50% of the mixture; however, the biodendrimer can be any suitable percentage of the mixture. Artificial bag 60 is adapted to allow light within the visible spectrum to pass therethrough. Preferably, capsular bag or capsule 60 has an exterior surface 62 and an interior surface 64, which defines an interior area or portion 66. Interior portion 66 can extend through the entire bag 60 or occupy a limited portion thereof. For example, portion 66 can be located in the rear portion of the bag, the front portion of the bag, the top portion of the bag, or the bottom portion of the bag or any other suitable location. Each location of portion 66 (i.e., rear, front, top and bottom) is relative to the location of a natural human eye, and is merely used herein for ease of understanding and is not meant to limit the present invention in any manner.

Additionally, portion 66 can occupy any percentage of the bag—i.e., substantially about 100% to substantially about 1%. The remainder of the bag can be filled with any suitable material, as described above, below, or in application Ser. No. 10/272,402, discussed above, or merely be defined by the thickness of the wall 68 between the exterior surface 62 and the interior surface 64. For example, the remainder of the bag can be filled with biodendrime, a mixture of biodendrimer and at least one other material, or any other suitable material. Preferably, biodendrimer is approximately 50% of the mixture; however, the biodendrimer can be any suitable percentage of the mixture.

Figure 10:
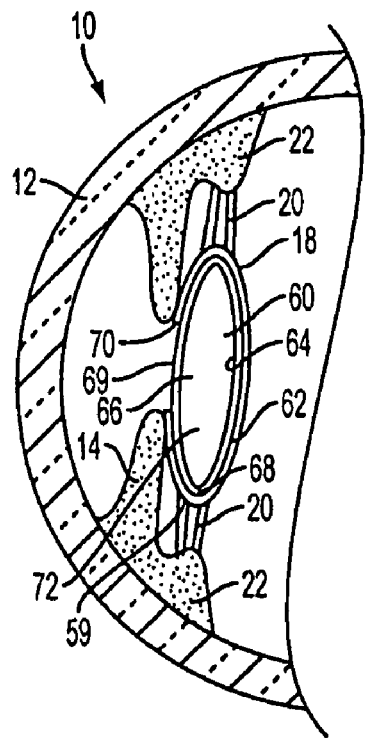
FIG. 10 is a side elevational view of a second embodiment of the present invention, wherein an artificial capsular bag is inserted into the natural capsular bag.

As shown specifically in FIG. 10, the central portion 69 of the natural capsular bag along the main optical axis is removed. The artificial capsular bag 60 is then inserted into the natural capsular bag 18 through opening 70. The artificial bag 60 can be placed inside of the natural bag 18 in any manner desired. For example, bag 60 can be merely positioned within bag 18, it can be positioned in bag 18 such that bag 18 is slightly stretched, it can be positioned, such that there is a "tight" fit (i.e., the artificial bag is tightly held within the natural bag, such that there is sufficient friction that the artificial bag cannot move or only move an insubstantial amount), or the artificial lens can be positioned within the natural bag using haptics any other type of device to prevent movement thereof. Further, the artificial bag 60 can be placed inside of the natural bag 18 such that there is space between some or the entire artificial bag 60 and the natural bag 18. Preferably, the space is filled with biodendrimer; however, the space can be filled with a mixture of biodendrimer and at least one other material, or any other suitable material, or left vacant if desired. Preferably, if a mixture occupies the space, biodendrimer is approximately 50% of the mixture; however, the biodendrimer can be any suitable percentage of the mixture.

By removing the central portion 69 of the natural capsular bag to form opening 70, the natural lens along the main optical axis is removed. This eliminates or substantially eliminates the possibility of capsular opacification of the lens in this area. However, it is noted that it is not necessary to remove the portion of the capsular bag at the main optical axis, and any size opening or aperture can be formed in any portion of the natural capsular bag that enables an artificial bag to be placed therein.

The capsular bag 60 is then filled with a liquid or synthetic material 72, which preferably includes monomers and a polymerization initiator, such as a photosensitizer in the same or substantially similar manner as the method and system described above for original capsular bag 18. Material 72 does not necessarily need to include both monomers and a photosensitizer, and may include only monomers or a photosensitizer, or any other material(s) that would enable the material to polymerize and/or change shape and/or volume. For example, material 72 can be biodendrimer or a mixture of biodendrimer and at least one other material. Preferably, biodendrimer is approximately 50% of the mixture; however, the biodendrimer can be any suitable percentage of the mixture. It is noted that the capsular bag 60 does not necessarily need to be filled after placement in the natural capsular bag and can be filled at any suitable time.

The synthetic material 72 is preferably the same or substantially similar to the materials described above or any material described in above mentioned U.S. application Ser. No. 10/272,402, the contents of which have previously been incorporated herein by reference. For example, the synthetic material 72 preferably contains loose monomers and an initiator that initiates polymerization of the loose monomers. In a preferred embodiment, the initiator is a photoinitiator so that when the material is exposed to the proper wavelength of light, preferably blue light, the initiator causes the loose monomers to polymerize. Initiators responsive to other sources of energy, such as heat or chemicals, may be used if desired.

The polymerization of the monomers caused by the initiators results in a lower concentration of monomers in the polymerized area. Through the principle of diffusion, loose monomers therefore migrate to the polymerized area, causing the polymerized area to swell. This allows the IOL to be adjusted to create perfect or substantially perfect (i.e., 20/20) vision. Suitable materials, and a more detailed discussion of their method of operation, are disclosed in U.S. Pat. No. 6,721,043 B2 to Platt et al., U.S. Pat. No. 6,749,632 B2 to Sandstedt et al., and U.S. Pat. App. No. 2003/0174375 A1 to Jethmalani et al, all of which are herein incorporated by reference in their entirety.

As described in the previous embodiments, changing the volume or shape of the IOL 59 can result in a decrease or in increase in volume or altered shape, thus changing the refractive properties of the lens to increase or decrease the diopter power. Additionally, the IOL can be adjusted multiple times as described above to "fine tune" the refractive properties of the IOL. Once the IOL has the desired refractive properties, the IOL can be completely polymerized as described above. Furthermore, the lens can be shaped, such that it forms a multifocal lens. The lens can have different portions that have different refractive properties to allow the eye to focus on both near and far objects. For example, the differing refractive properties can be substantially ring-shaped concentric to each other or positioned at any other place or position on the lens.

Figure 11:
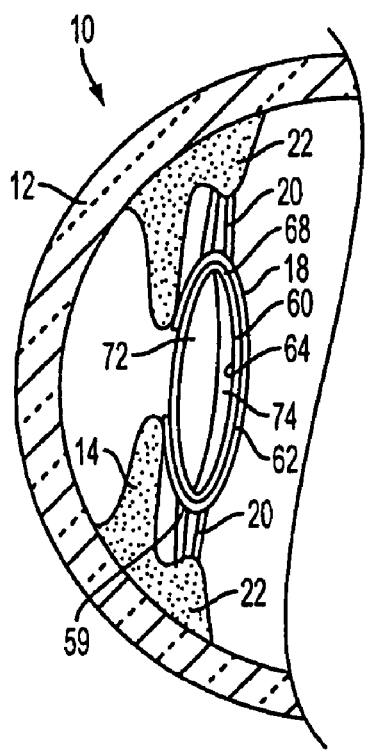
FIG. 11 is a side elevational view of a third embodiment of the present invention, wherein only the rear portion of the intraocular lens has been polymerized.

Additionally, as shown in FIG. 11, a portion 74, such as the rear portion of liquid or material 72, can be polymerized prior to insertion inside of the natural capsular bag 18. However, it is noted that the portion 74 to be polymerized does not necessarily need to be the rear portion and can be any portion desired, including a front portion or a front and rear portion. By polymerizing portion 74 prior to insertion into capsular bag 18, the artificial bag 60 has rigidity that can help shape and/or support the natural bag in a predetermined manner, thus facilitating the forming of the desired shape of the natural and/or artificial bags.

Furthermore, portion 74 need not necessarily be a liquid that is polymerized as discussed above, but can be a solid or substantially solid material that is generally used for forming conventional IOLs or any other suitable material. For example, portion 74 can be a separate collagen material (or any other suitable material) added to the interior or exterior of the bag or it may simply by a portion of wall between the exterior surface 62 and the interior surface 64. Further, portion 74 can be biodendrimer or a mixture of biodendrimer and at least one other material. Preferably, biodendrimer is approximately 50% of the mixture; however, the biodendrimer can be any suitable percentage of the mixture.

Additionally, the capsular bag 60 can be positioned adjacent to or coupled to a conventional IOL. For example, the capsular bag 60 can be affixed to the front surface or rear surface of a conventional IOL prior to, during or after insertion of the IOL in the natural capsular bag 18.

Figure 12:
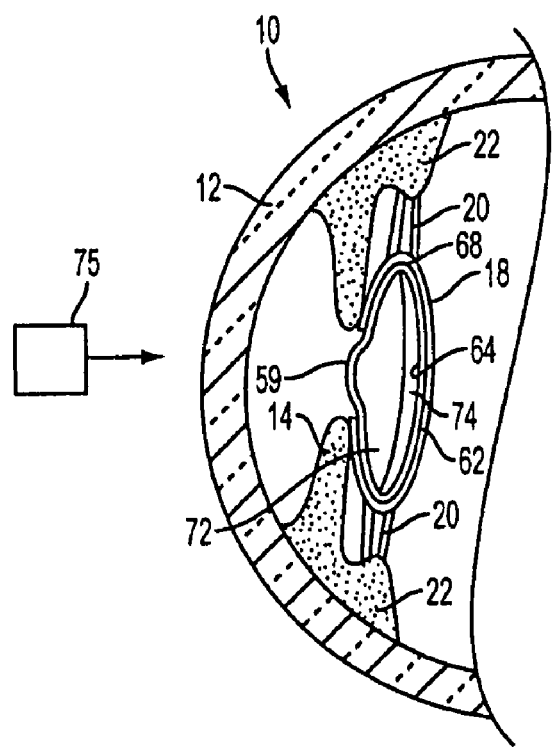
FIG. 12 is a side elevational view of the embodiment of FIG. 11 showing a portion of the intraocular lens increasing in volume when exposed to laser light.
Figure 13:
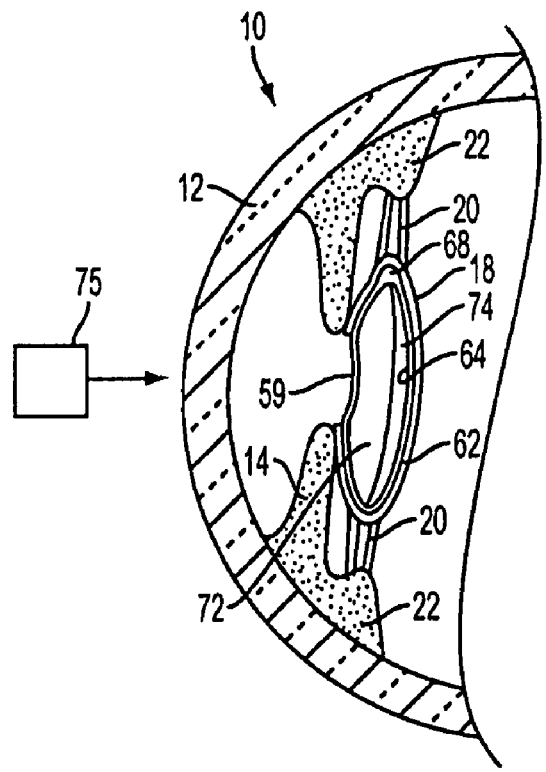
FIG. 13 is a side elevational view of the embodiment of FIG. 11 showing a portion of the intraocular lens decreasing in volume when exposed to laser light.

As shown in FIGS. 12 and 13, and as discussed above, changing the volume or shape of the front portion of the IOL 59 by exposing the unpolymerized material to a light (such as from laser 75 or any other suitable light source) will result in a decrease or an increase in volume or an altered shape, thus changing the refractive properties of the lens to increase or decrease the diopter power. Additionally, the IOL can be adjusted multiple times as described above to "fine tune" the refractive properties of the IOL. Once the IOL has the desired refractive properties, the IOL can be completely polymerized as described above. Furthermore, the lens can be shaped, such that it forms a multifocal lens. The lens can have different portions that have different refractive properties to allow the eye to focus on both near and far objects. For example, the differing refractive properties can be substantially ring-shaped concentric to each other or positioned at any other place or position on the lens. It is noted that as with the other embodiments described above and in application Ser. No. 10/272,402, the polymerizing initiator can initiate polymerization when exposed to light, laser light, a chemical or any other suitable device and/or method.

Figure 14:
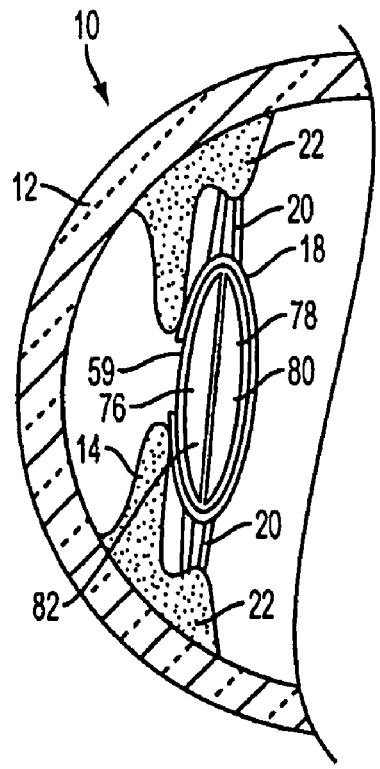
FIG. 14 is a side elevational view of a fourth embodiment of the present invention, wherein the interior of the artificial bag is divided into two portions.

Additionally, as shown in FIG. 14, the artificial capsular bag 60 can be divided into two interior portions, a first portion or chamber 76 and a second portion or chamber 78. Preferably, first portion 76 is located in the front part of bag 60 (i.e., closer to the anterior chamber or the iris) and second portion 78 is located in the rear or back portion of the bag (i.e., farther from the anterior chamber of iris).

Prior to insertion into the natural bag 18, the rear chamber preferably is filled with liquid or material 80, which preferably includes monomers and a polymerization initiator, such a photosensitizer in the same or substantially similar manner as the method and system described above for each of the other embodiments. Liquid 80 does not necessarily need to include both monomers and a photosensitizer, and may include only monomers or a photosensitizer, or any other material that would enable the material to polymerize and or change shape and/or volume. Further, liquid 80 can be biodendrimer or a mixture of biodendrimer and at least one other material. Preferably, biodendrimer is approximately 50% of the mixture; however, the biodendrimer can be any suitable percentage of the mixture.

Figure 15:
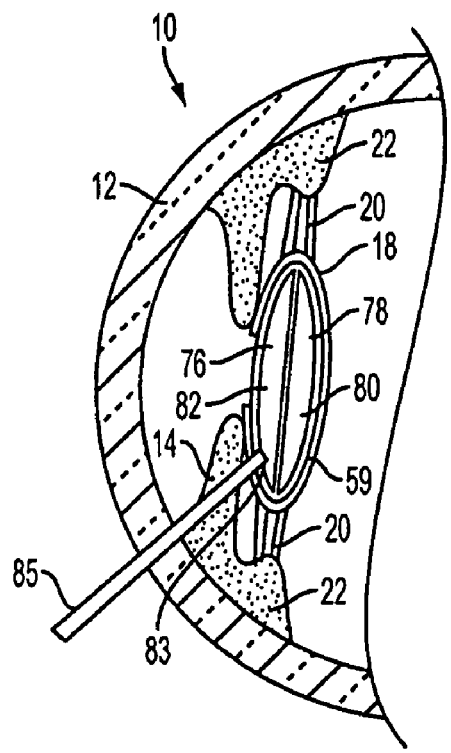
FIG. 15 is a side elevational view of a the embodiment of FIG. 14 showing the insertion of a liquid into one the interior chambers of the artificial bag.

As shown in FIG. 15, the front chamber is preferably filled with a liquid polymer or material 82 suitable for insertion into the eye using a cannula 85 or any other suitable method or device. The liquid polymer can be inserted into chamber 76 through an opening 83 or a small self sealing membrane after implantation of the bag 60. It is noted that both liquid 80 and liquid 82 can be inserted into the bag at any time desired. For example, each liquid can be inserted before, after or during the surgical procedure. Liquid 82 can be biodendrimer or a mixture of biodendrimer and at least one other material. Preferably, biodendrimer is approximately 50% of the mixture; however, the biodendrimer can be any suitable percentage of the mixture.

It is noted that it is not necessary to fill the rear chamber with liquid 80 and the front chamber with liquid 82. This positioning of the respective liquids is merely the preferred embodiment and either of the liquids can be placed in either of the chambers. Furthermore it is noted that chambers 76 and 78 can have substantially the same volume or can have any volume desired. For example, one chamber can be larger or smaller than the other volume. Additionally, the overall volume of both chambers can occupy any amount of the volume of IOL 59 desired. For example the overall volume of chambers 76 and 78 can occupy from about 1% of the overall volume for IOL 59 to about 99%.

Figure 16:
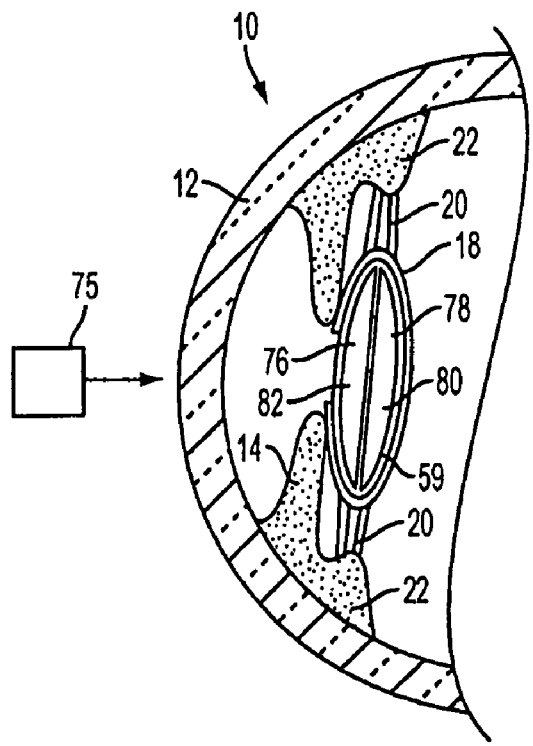
FIG. 16 is a side elevational view of the embodiment of FIG. 14 showing a portion of the intraocular lens increasing in volume when exposed to laser light.
Figure 17:
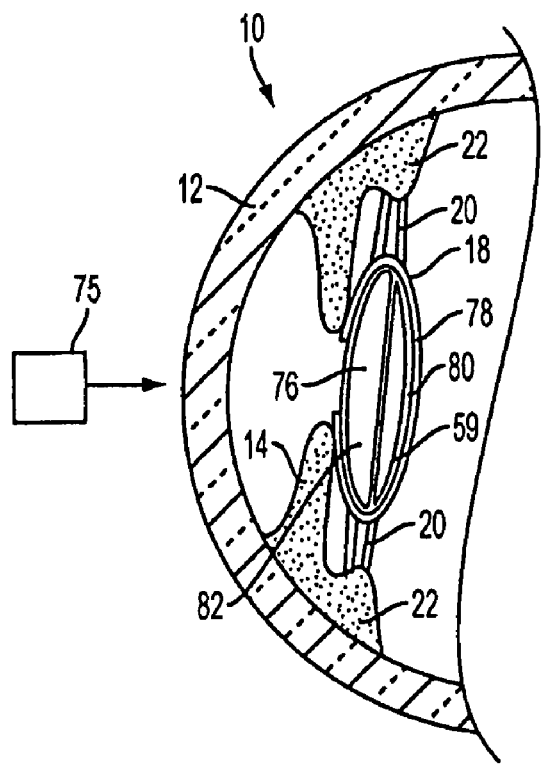
FIG. 17 is a side elevational view of the embodiment of FIG. 14 showing a portion of the intraocular lens decreasing in volume when exposed to laser light.

As shown in FIGS. 16 and 17, and as discussed above, changing the volume or shape of the rear chamber 78 of the IOL 59 by exposing the unpolymerized material to a light (such as from laser 75 or any other suitable light source) will result in a decrease or an increase in volume or change in shape, thus changing the refractive properties of the lens to increase or decrease the diopter power. Furthermore, the lens can be shaped, such that it forms a multifocal lens. The lens can have different portions that have different refractive properties to allow the eye to focus on both near and far objects. For example, the differing refractive properties can be substantially ring-shaped concentric to each other or positioned at any other place or position on the lens. Additionally, the IOL can be adjusted multiple times as described above to "fine tune" the refractive properties of the IOL. Once the IOL has the desired refractive properties, the IOL can be completely polymerized as described above. It is noted that as with the other embodiments described above and in application Ser. No. 10/272,402, the polymerizing initiator can initiate polymerization when exposed to light, laser light, a chemical or any other suitable device and/or method.

Figure 18:
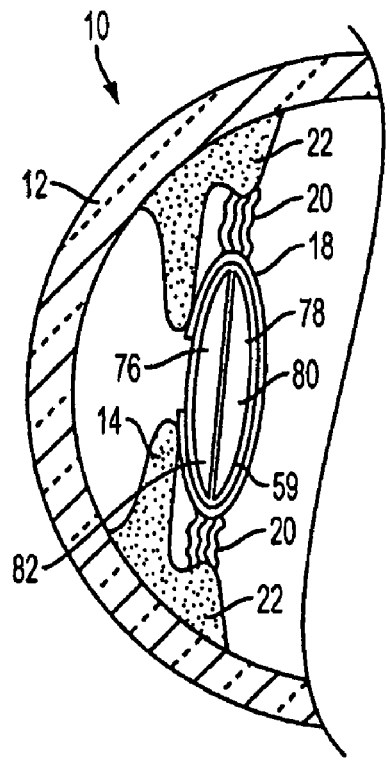
FIG. 18 is a side elevational view of the embodiment of FIG. 14 showing accommodation.

As shown in FIG. 18, this embodiment allows the lens system, particularly the bag 60 to remain flexible, and thus act like a natural lens. In other words, when the eye attempts to focus on a near object (i.e., accommodate), the lens zonules loosen the natural bag, which in turn loosens the artificial bag. Each bag 18 and 60 then bulges slightly in the center. This bulging increases the refractive power of the natural lens. Conversely when the zonules tighten, each bag tends to be stretched, decreasing the refractive power. That is, when a portion of the artificial bag 60 is filled with liquid polymer 82, the artificial bag 60 and thus the natural bag 18 remain flexible after implantation. Therefore, the process of accommodation bulges the central portion of the bag, which increases the convexity of the front portion of the lens, increasing the refractive power of the lens for near vision.

Additionally, since the liquid is a polymer any exposure to light or a polymerizing agent does not polymerize the this material; however, as described above, the material 80 can be subject to exposure to different energies that would increase or decrease the volume or change the shape and/or polymerize a portion or the entire volume thereof, as for any of the embodiments describe above or in application Ser. No. 10. 10/272,402.

Furthermore, the rear chamber or portion 78 can be divided into two areas or portions in a manner similar to the embodiment described in FIGS. 11-13 and FIGS. 14-18, thus forming three chambers or areas with the artificial bag 60. In this embodiment, a first portion would be filled with a material, such as liquid 82, the second portion would be filled with a material, such as material 80, and the third portion would include a polymerized material as described from FIGS. 11-13. Therefore as described above, the lens can have rigidity for insertion into the capsular bag 18 and have the volume or shape thereof changed while inside the capsular bag to achieve the desired refractive power.

Figure 19:
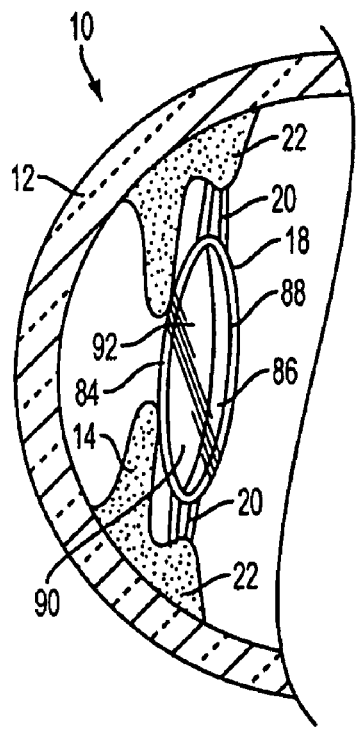
FIG. 19 is a side elevational view of a fifth embodiment of the present invention, wherein a portion of the interior of the capsular bag is coated and the remainder of the capsular bag is filled with biodendrimer or a mixture of biodendrimer and at least one other material.

FIG. 19 shows another embodiment of the present invention, wherein an IOL 84 is formed by coating a portion 86 of capsular bag 18 with a synthetic material 88. The synthetic material 88 is preferably a silicone based material which is un-polymerized as described above and shown in FIG. 4; however, the synthetic material 88 can be any suitable material. Preferably, the synthetic material 88 contains loose monomers and an initiator that initiates polymerization of the loose monomers. In a preferred embodiment, the initiator is a photoinitiator so that when the material is exposed to the proper wavelength of light, preferably blue light, the initiator causes the loose monomers to polymerize. Initiators responsive to other sources of energy, such as heat or chemicals, may be used if desired.

As above, the polymerization of the monomers caused by the initiators results in a lower concentration of monomers in the polymerized area. Through the principle of diffusion, loose monomers therefore migrate to the polymerized area, causing the polymerized area to swell. Some suitable materials, and a more detailed discussion of their method of operation, are disclosed in U.S. Pat. No. 6,721,043 B2 to Platt et al., U.S. Pat. No. 6,749,632 B2 to Sandstedt et al., and U.S. Pat. App. No. 2003/0174375 A1 to Jethmalani et al, all of which were incorporated by reference in their entirety above.

It should be noted that though FIG. 19 shows portion 86 of capsular bag 18 being a rear portion, any portion, including but not limited to the front, top, bottom, sides, or any combination thereof, can be coated with synthetic material 88. The portion 86 of capsular bag 18 can be coated using any suitable method, including but not limited to injection though a cannula.

The space 90 within the capsular bag 18 after the portion 86 is coated is preferably filled with biodendrimer 92; however, the space 90 can be filled with a mixture of biodendrimer and at least one other material. If the space 90 is filled with a mixture of biodendrimer and at least one other material, biodendrimer is preferably approximately 50% of the mixture; however, biodendrimer can be any suitable percentage of the mixture. The space 90 can be filled with biodendrimer 92 using any suitable method, including but not limited to injection though a cannula.

As discussed above, the refractive properties of IOL 84 can be altered by changing the volume of the portion 86 of the IOL 84 by exposing the unpolymerized material to a light. Furthermore, the lens can be shaped, such that it forms a multi-focal lens. The lens can have different portions that have different refractive properties to allow the eye to focus on both near and far objects. For example, the differing refractive properties can be substantially ring-shaped concentric to each other or positioned at any other place or position on the lens. Additionally, the IOL 84 can be adjusted multiple times as described above to "fine tune" the refractive properties of the IOL 84. Once the IOL has the desired refractive properties, the IOL can be completely polymerized as also described above. It is noted that as with the other embodiments described above and in application Ser. No. 10/272,402, the polymerizing initiator can initiate polymerization when exposed to light, laser light, a chemical or any other suitable device and/or method.

Similar to other embodiments, this embodiment allows the lens system to remain flexible, and thus act like a natural lens. In other words, when the eye attempts to focus on a near object (i.e., accommodate), the lens zonules loosen the capsular bag 18. The bag 18 then bulges slightly in the center, and this bulging increases the refractive power of the natural lens. Conversely when the zonules tighten, the bag tends to be stretched, decreasing the refractive power. That is, when a space 90 of the capsular bag 18 is filled with biodendrimer 92, or a mixture of biodendrimer and at least one other suitable material, the capsular bag 18 remains flexible after implantation of IOL 84. Therefore, the process of accommodation bulges the central portion of the bag 18, which increases the convexity of the front portion of the lens, increasing the refractive power of the lens for near vision.

Figure 20:
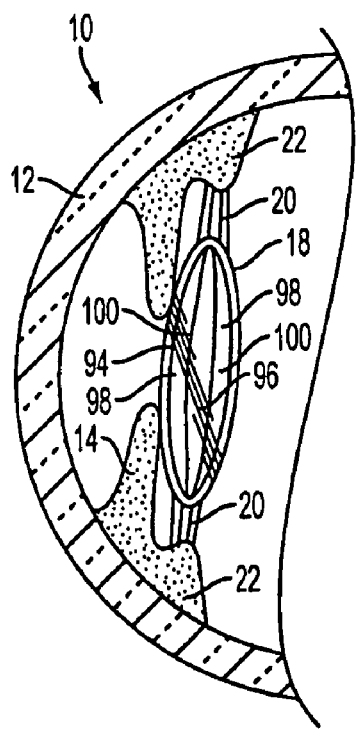
FIG. 20 is a side elevational view of a sixth embodiment of the present invention, wherein an artificial lens is inserted into the capsular bag and the remainder of the capsular bag is filled with biodendrimer or a mixture of biodendrimer and at least one other material.

FIG. 20 shows still another embodiment of the present invention, wherein an IOL 94 is formed by inserting an artificial lens 96 into the capsular bag 18. The artificial lens 96 is preferably silicone based; however, the artificial lens 96 can be any suitable material, including biodendrimer. Preferably, the artificial lens 96 includes loose monomers and an initiator that initiates polymerization of the loose monomers. In a preferred embodiment, the initiator is a photoinitiator so that when the material is exposed to the proper wavelength of light, preferably blue light, the initiator causes the loose monomers to polymerize. Initiators responsive to other sources of energy, such as heat or chemicals, may be used if desired.

As above, the polymerization of the monomers caused by the initiators results in a lower concentration of monomers in the polymerized area. Through the principle of diffusion, loose monomers therefore migrate to the polymerized area, causing the polymerized area to swell. Some suitable materials, and a more detailed discussion of their method of operation, are disclosed in U.S. Pat. No. 6,721,043 B2 to Platt et al., U.S. Pat. No. 6,749,632 B2 to Sandstedt et al., and U.S. Pat. App. No. 2003/0174375 A1 to Jethmalani et al, all of which were incorporated by reference in their entirety above.

It should be noted that though FIG. 20 shows the artificial lens 96 being placed in the center of the capsular bag 18, the artificial lens can be placed in any location within the capsular bag 18, including but not limited to the front or back. Preferably, the artificial lens 96 is placed in the capsular bag 18 by rolling or folding the lens 96 and inserting the lens 96 though an opening in the capsular bag 18; however, the lens 96 can be inserted using any suitable technique. Once inside the bag 18, the lens 96 preferably unrolls or unfolds automatically; however, the lens 96 can be unrolled or unfolded manually, if desired. Preferably, the lens is sized and configured to frictionally fit within the capsular bag, such that the lens is immobile or substantially immobile; however the lens can be positioned and/or fixed in position in any suitable manner.

The space 98 within the capsular bag 18 after the lens 96 is inserted is preferably filled with biodendrimer 100; however, the space 98 can be filled with a mixture of biodendrimer and at least one other material. If the space 98 is filled with a mixture of biodendrimer and at least one other material, biodendrimer is preferably approximately 50% of the mixture; however, biodendrimer can be any suitable percentage of the mixture. The space 98 can be filled with biodendrimer 100 using any suitable method, including but not limited to injection though a cannula.

As discussed above, the refractive properties of IOL 94 can be altered by changing the volume of the lens 96 of the IOL 94 by exposing the unpolymerized material to a light. Furthermore, the lens can be shaped, such that it forms a multifocal lens. The lens can have different portions that have different refractive properties to allow the eye to focus on both near and far objects. For example, the differing refractive properties can be substantially ring-shaped concentric to each other or positioned at any other place or position on the lens. Additionally, the IOL 94 can be adjusted multiple times as described above to "fine tune" the refractive properties of the IOL 94. Once the IOL has the desired refractive properties, the IOL can be completely polymerized as also described above. It is noted that as with the other embodiments described above and in application Ser. No. 10/272,402, the polymerizing initiator can initiate polymerization when exposed to light, laser light, a chemical or any other suitable device and/or method.

Similar to other embodiments, this embodiment allows the lens system to remain flexible, and thus act like a natural lens. In other words, when the eye attempts to focus on a near object (i.e., accommodate), the lens zonules loosen the capsular bag 18. The bag 18 then bulges slightly in the center, and this bulging increases the refractive power of the natural lens. Conversely when the zonules tighten, the bag tends to be stretched, decreasing the refractive power. That is, when a space 98 of the capsular bag 18 is filled with biodendrimer 100, or a mixture of biodendrimer and at least one other suitable material, the capsular bag 18 remains flexible after implantation of IOL 94. Therefore, the process of accommodation bulges the central portion of the bag 18, which increases the convexity of the front portion of the lens, increasing the refractive power of the lens for near vision.

Figure 21:
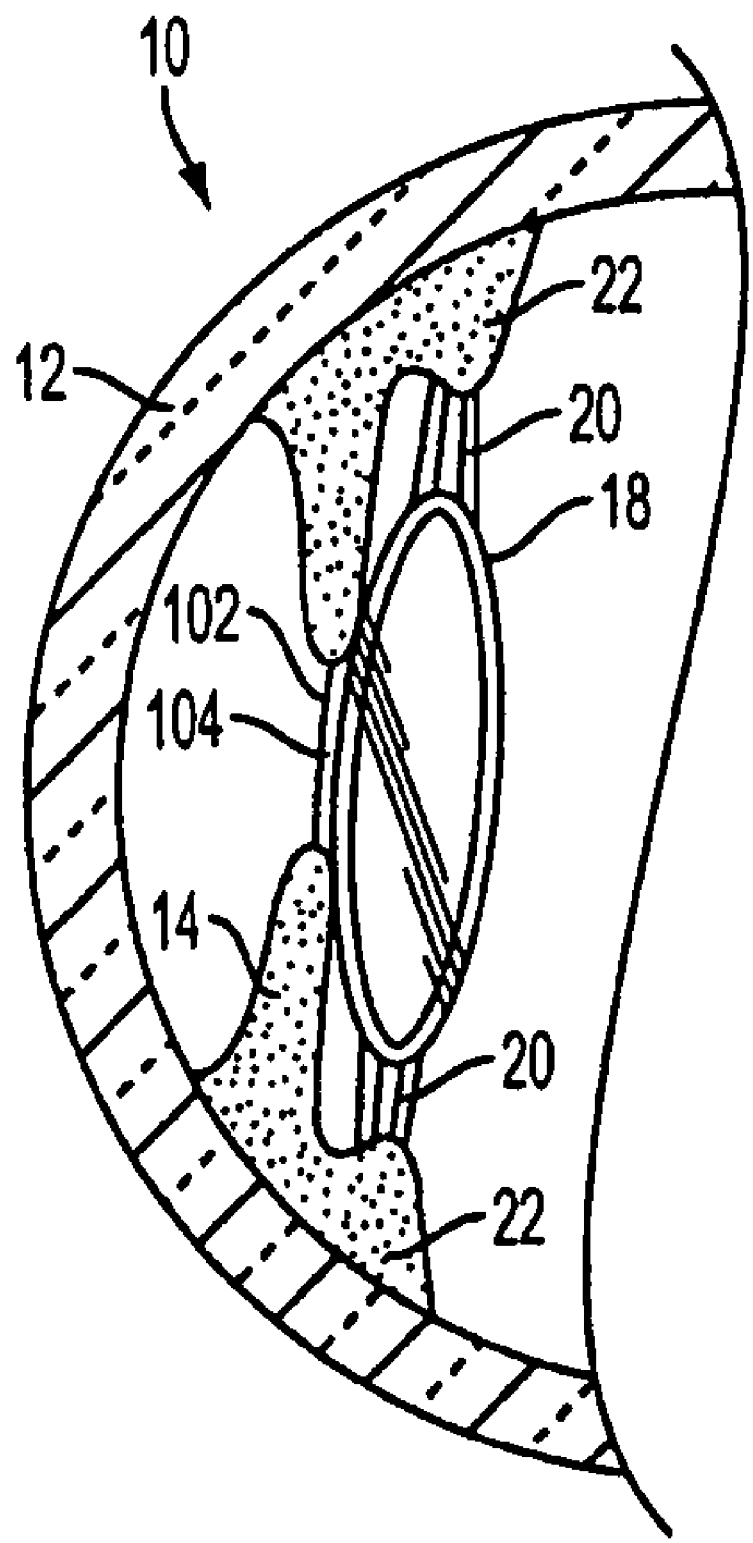
FIG. 21 is a side elevational view of a seventh embodiment of the present invention, wherein an exterior surface of the capsular bag is coated with biodendrimer or a mixture of biodendrimer and at least one other material.

FIG. 21 shows still another embodiment of the present invention, wherein an IOL 102 is formed by coating the exterior of the capsular bag 18 with a synthetic material 104. The synthetic material 104 is preferably a mixture that includes biodendrimer and an un-polymerized material; however, the synthetic material 104 can be any suitable material. Preferably, the un-polymerized material is an un-polymerized silicone based material; however, the material can be any suitable un-polymerized material. Further, the synthetic material 104 is preferably a mixture of approximately 50% biodendrimer and approximately 50% an un-polymerized material; however, the synthetic material 104 can have any suitable percentage of biodendrimer, un-polymerized material or other material.

The synthetic material 104 can be selectively polymerized, as discussed above, to adjust the optical properties of the eye. The adjustment process can be repeated until the desired corrective capabilities have been programmed into the lens 102. Once satisfied with the optical properties, the entire lens 102 is irradiated with an appropriate wavelength of light to polymerize the entire unpolymerized material in the lens, thereby fixing the refractive power of the lens 102.

After this final polymerization of the lens 102, the lens 102 takes on a gel-like consistency that approximates the function of a crystalline lens. The lens 102 therefore is capable of providing accommodation. It should be noted that removal of the original crystalline lens is not necessary for formation of the IOL 102 by coating the exterior of the capsular bag 18 with the synthetic material 104.

Figure 22:
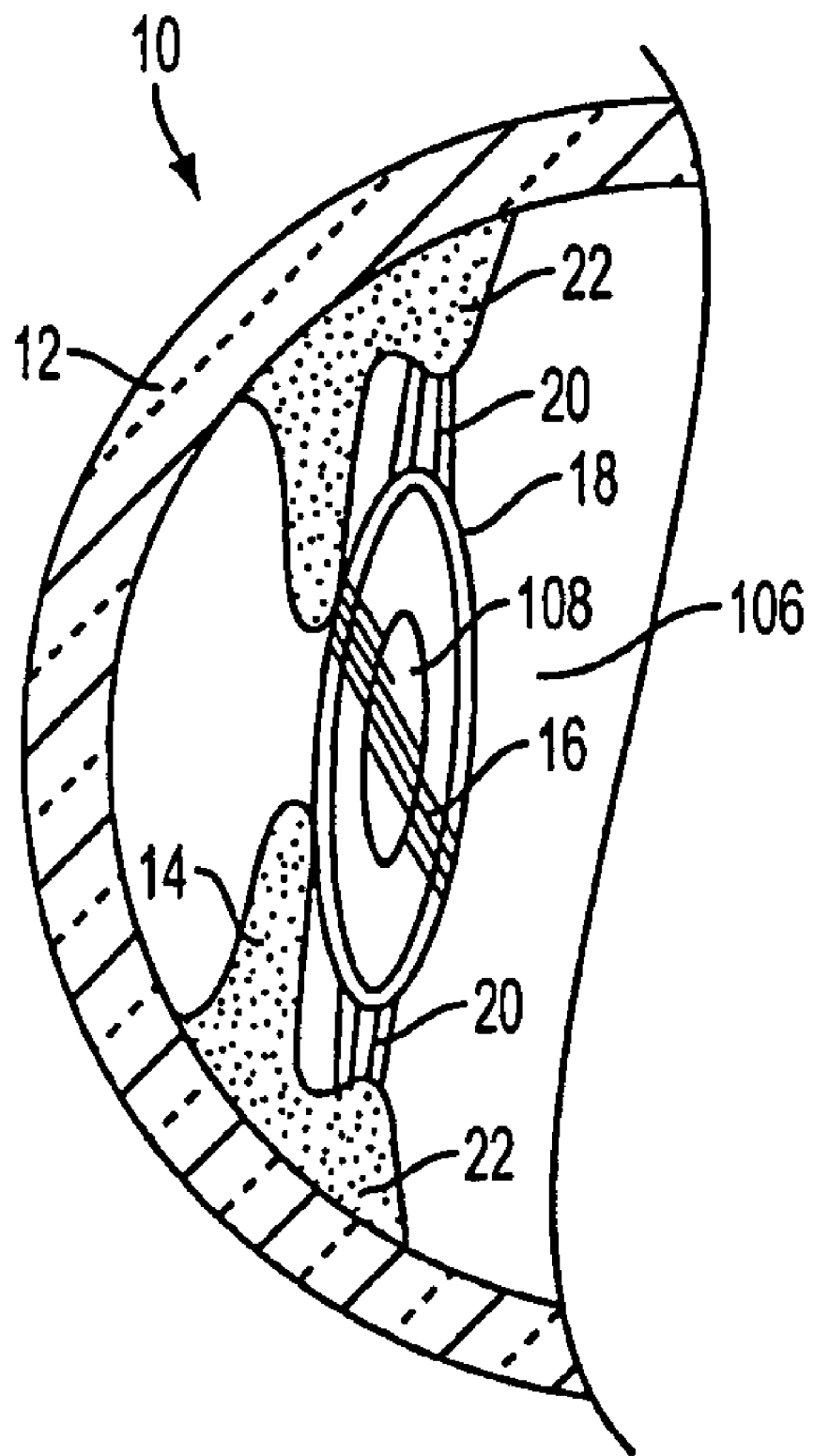
FIG. 22 is a side elevational view of an eighth embodiment of the present invention, wherein a portion of the crystalline lens of an eye is removed and replaced with biodendrimer or a mixture of biodendrimer and at least one other material.

FIG. 22 shows still another embodiment of the present invention, wherein an IOL 106 is formed by removing only a portion of the crystalline lens 16. The portion can be removed using any suitable technique, including but not limited to the techniques described above for removing the entire crystalline lens. Once the portion is removed, the remaining cavity is at least partly filled with a synthetic material 108. The synthetic material 108 is preferably a mixture that includes biodendrimer and an un-polymerized material; however, the synthetic material 108 can be any suitable material. Preferably, the un-polymerized material is an un-polymerized silicone based material; however, the material can be any suitable un-polymerized material, including biodendrimer. Further, the synthetic material 108 is preferably a mixture of approximately 50% biodendrimer and approximately 50% an un-polymerized material; however, the synthetic material 108 can have any suitable percentage of biodendrimer, un-polymerized material or other material.

The synthetic material 108 can be selectively polymerized, as discussed above, to adjust the optical properties of the eye. The adjustment process can be repeated until the desired corrective capabilities have been programmed into the lens 106. Once satisfied with the optical properties, the entire lens 106 is irradiated with an appropriate wavelength of light to polymerize the entire unpolymerized material in the lens, thereby fixing the refractive power of the lens 106. After this final polymerization of the lens 106, the lens 106 retains the ability to accommodate.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A method of replacing a natural lens in an eye, comprising the steps of:
   removing at least a portion of the natural lens while leaving the capsular bag substantially intact;
   injecting a synthetic material into the capsular bag to form an artificial lens including loose monomers;
   placing biodendrimer within the capsular bag; and
   selectively exposing portions of the artificial lens to an energy source to alter the refractive properties of the artificial lens to change its volume to a predetermined volume to correct a predetermined refractive error when exposed to an energy source.

2. The method of claim 1, further comprising the step of:
   removing a portion of the capsular bag along the main optical axis.

3. The method of claim 1, wherein placing biodendrimer within the capsular bag includes placing a mixture of biodendrimer and at least one other material within the artificial bag.

4. The method of claim 3, wherein biodendrimer is approximately fifty percent of the mixture.

5. The method of claim 1, further comprising the steps of:
   inserting an artificial bag within the capsular bag; and
   injecting the synthetic material into the artificial bag to form the artificial lens, the synthetic material having a polymerization initiator.

6. The method of claim 1, wherein the energy source is light.

7. The method of claim 5, wherein the step of placing biodendrimer within the capsular artificial bag includes injecting biodendrimer into the artificial bag.

8. The method of claim 5, wherein the step of placing biodendrimer within the capsular bag includes injecting biodendrimer between the artificial bag and the capsular bag.

9. The method of claim 5, wherein the artificial bag includes biodendrimer.

10. The method of claim 1, further comprising the step of:
    exposing substantially the entire artificial lens to an energy source to polymerize substantially all of the loose monomers, thereby fixing the refractive power of the synthetic material.

11. The method of claim 5, wherein the step of inserting an artificial bag includes inserting an artificial bag having a first internal chamber and a second internal chamber.

12. The method of claim 11, wherein said first internal chamber includes a polymerized material, and said step of injecting a synthetic material into the artificial bag includes injecting said synthetic material into said second chamber.

13. The method of claim 12, wherein the polymerized material is biodendrimer.

14. The method of claim 12, wherein the step of placing biodendrimer within the capsular bag includes injecting biodendrimer into said second chamber.

15. The method of claim 5, wherein a portion of said artificial bag includes a polymerized material.

16. The method of claim 5, wherein the step of selectively exposing portions of the artificial lens to an energy source includes forming a multifocal lens.

17. The method of claim 1, further comprising the step of:
coating a portion of the capsular bag with a synthetic material, the synthetic material having loose monomers and a polymerization initiator so that the synthetic material changes its volume when exposed to an energy source.

18. The method of claim 17, wherein the step of placing biodendrimer within the capsular bag includes filling the remaining portion of the capsular bag with a material, wherein the material includes biodendrimer.

19. The method of claim 1, further comprising the step of:
inserting a lens into the capsular bag, the lens including loose monomers and a polymerization initiator so that the synthetic material changes the shape of the lens when the synthetic material is exposed to an energy source.

20. The method of claim 19, wherein the step of placing biodendrimer within the capsular bag includes filling the remaining portion of the capsular bag with a material, wherein the material includes biodendrimer.

21. A method of modifying the optical properties of an eye, comprising the steps of:
coating at least a portion of an external surface of a capsular bag with a synthetic substance, wherein the synthetic substance includes biodendrimer and an unpolymerized material positioned having loose monomers and a polymerization initiator so that the unpolymerized material changes the shape of the flexible capsule when exposed to an energy source.

22. An intraocular lens, comprising:
a flexible capsule adapted to be inserted into the natural lens capsular bag;
a polymerized portion, including biodendrimer, positioned within said flexible capsule; and
an unpolymerized material positioned within said flexible capsule, and having loose monomers and a polymerization initiator so that the unpolymerized material changes the shape of the flexible capsule when exposed to an energy source;
wherein said unpolymerized material is capable of changing the shape of the flexible capsule, such that the flexible capsule is multifocal.

* * * * *